United States Patent [19]

Uchida et al.

[11] Patent Number: 5,202,055

[45] Date of Patent: * Apr. 13, 1993

[54] ALKENYL ETHER COMPOUND AND A COMPOSITION CONTAINING THE SAME

[75] Inventors: Manabu Uchida; Kisei Kitano; Shinichi Sawada; Keiko Uchida, all of Ichiharashi, Japan

[73] Assignee: Chisso Corporation, Osaka, Japan

[*] Notice: The portion of the term of this patent subsequent to Apr. 7, 2009 has been disclaimed.

[21] Appl. No.: 407,286

[22] Filed: Sep. 14, 1989

[30] Foreign Application Priority Data

Sep. 19, 1988 [JP] Japan .................. 63-234531

[51] Int. Cl.$^5$ .................. C09K 19/30; C07C 255/00
[52] U.S. Cl. .................. 252/299.63; 558/423
[58] Field of Search .................. 252/299.01, 299.63; 558/423

[56] References Cited

U.S. PATENT DOCUMENTS

| | | | |
|---|---|---|---|
| 4,468,340 | 8/1984 | Inoue et al. | 252/299.63 |
| 4,676,604 | 6/1987 | Petrzilka | 252/299.63 |
| 4,709,030 | 11/1987 | Petrzilka et al. | 252/299.63 |
| 4,770,503 | 9/1988 | Buchecker et al. | 252/299.63 |
| 4,846,998 | 7/1989 | Pohl et al. | 252/299.63 |
| 4,874,543 | 10/1989 | Yoshida | 252/299.63 |
| 4,943,384 | 7/1990 | Sucrow et al. | 252/299.63 |
| 5,013,478 | 5/1991 | Petrzilka | 252/299.63 |
| 5,030,383 | 7/1991 | Scheuble et al. | 252/299.63 |
| 5,032,312 | 7/1991 | Kelly | 252/299.63 |

FOREIGN PATENT DOCUMENTS

| | | | |
|---|---|---|---|
| 360080 | 3/1990 | European Pat. Off. | 558/423 |
| 3601452 | 7/1987 | Fed. Rep. of Germany . | |
| 58-59956 | 4/1983 | Japan . | |
| 59-176221 | 5/1984 | Japan . | |

*Primary Examiner*—Robert L. Stoll
*Assistant Examiner*—Philip Tucker
*Attorney, Agent, or Firm*—Leydig, Voit & Mayer

[57] ABSTRACT

A compound and a liquid crystal composition containing the compound are provided, which compound, when added to a nematic liquid crystal composition, increases the dielectric anisotropy value, lowers its threshold voltage and raises the ratios of elastic constants and hence makes steep the voltage-transmittance characteristic, which compound is an alkenyl ether compound expressed by the formula

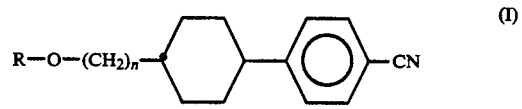

wherein R is a 2-8C alkyl group having a double bond at its end or a double bond of trans configuration at an optional position and n is 0 to 4.

7 Claims, No Drawings

ALKENYL ETHER COMPOUND AND A COMPOSITION CONTAINING THE SAME

BACKGROUND OF THE INVENTION

1. Field of the Invention

This invention relates to a novel organic compound and more particularly it relates to an alkenyl ether compound useful as a liquid crystal component and a liquid crystal composition containing the same.

2. Description of the Related Art

Liquid crystals have recently been becoming more and more important as a dielectric for liquid crystal display devices and the reason consists in an electrooptical effect based on the dielectric anisotropy and the optical anisotropy of liquid crystalline substances. Liquid crystal display modes based on liquid crystals include dynamic scattering mode, phase transition mode, DAP mode, guest-host mode, TN mode using a 90° twist cell, STN or SBE mode using a 180°–270° twist cell, etc. It is necessary for liquid crystals used for liquid crystal displays to satisfy a number of necessary characteristics such as a broad mesomorphic range, a good stability to environmental factors (e.g. moisture, heat, air, light, electricity, etc.), colorless, values of physical properties suitable to display modes used, etc. For example, in the case of a SBE mode, a characteristic required therefor consists in that the voltage-transmittance characteristic ($\gamma$ characteristic) is steep. As a parameter expressing the steepness of the $\gamma$ characteristic, there are elastic constant ratios $K_{33}/K_{11}$ and $K_{33}/K_{22}$, and when the values of the elastic constant ratios $K_{33}/K_{11}$ and $K_{33}/K_{22}$ are high, the $\gamma$ characteristic becomes steep (Nakagome et al, the 12th Liquid Crystal Symposium, 3-F13 (1987)).

Herein, $K_{11}$ refers to an elastic constant of splay, $K_{22}$ refers to an elastic constant of twist and $K_{33}$ refers to an elastic constant of bend.

At present, there is no single compound satisfying all of these necessary characteristics; hence actually, there have been used liquid crystal mixtures obtained by mixing several kinds of liquid crystal compounds or by mixing compounds having latent liquid crystallinity or non-crystalline compounds with several kinds of liquid crystal compounds. Thus, it is also required that liquid crystals have a good, compatibility with other liquid crystal compounds.

SUMMARY OF THE INVENTION

The object of the present invention is to provide a liquid crystalline compound and a liquid crystal composition provided with various characteristics as described above. The liquid crystalline compound referred to herein includes not only compounds exhibiting usual liquid crystal phases, but also those exhibiting apparently no liquid crystal phase by themselves, but when dissolved in other liquid crystal compounds, effectively functioning in a certain aspect having liquid crystal behavior.

The present invention resides in an alkenyl ether compound expressed by the formula

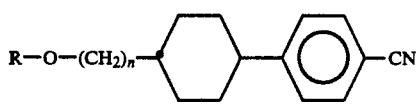

(I)

wherein R represents an alkenyl group of 2 to 8 carbon atoms having a double bond at its end or a double bond of trans configuration in any other position and n represents an integer of 0 to 4.

DETAILED DESCRIPTION OF PREFERRED EMBODIMENTS

The compound of the formula (I) of the present invention will be concretely exemplified below.

Case of n=0 in the formula (I)

4-(Trans-4'-vinyloxycyclohexyl)benzonitrile
4-[Trans-4'-(trans-1-propenyloxy)cyclohexyl]benzonitrile
4-(Trans-4'-allyloxycyclohexyl)benzonitrile
4-[Trans-4'-(trans-1-butenyloxy)cyclohexyl]benzonitrile
4-[Trans-4'-(trans-2-butenyloxy)cyclohexyl]benzonitrile
4-[Trans-4'-(3-butenyloxy)cyclohexyl]benzonitrile
4-[Trans-4'-(trans-1-pentenyloxy)cyclohexyl]benzonitrile
4-[Trans-4'-(trans-2-pentenyloxy)cyclohexyl]benzonitrile
4-[Trans-4'-(trans-3-pentenyloxy)cyclohexyl]benzonitrile
4-[Trans-4'-(4-pentenyloxy)cyclohexyl]benzonitrile
4-[Trans-4'-(trans-1-hexenyloxy)cyclohexyl]benzonitrile
4-[Trans-4'-(trans-2-hexenyloxy)cyclohexyl]benzonitrile
4-[Trans-4'-(trans-3-hexenyloxy)cyclohexyl]benzonitrile
4-[Trans-4'-(trans-4-hexenyloxy)cyclohexyl]benzonitrile
4-[Trans-4'-(5-hexenyloxy)cyclohexyl]benzonitrile
4-[Trans-4'-(trans-1-heptenyloxy)cyclohexyl]benzonitrile
4-[Trans-4'-(trans-2-heptenyloxy)cyclohexyl]benzonitrile
4-[Trans-4'-(trans-3-heptenyloxy)cyclohexyl]benzonitrile
4-[Trans-4'-(trans-4-heptenyloxy)cyclohexyl]benzonitrile
4-[Trans-4'-(trans-5-heptenyloxy)cyclohexyl]benzonitrile
4-[Trans-4'-(6-heptenyloxy)cyclohexyl]benzonitrile
4-[Trans-4'-(trans-1-octenyloxy)cyclohexyl]benzonitrile
4-[Trans-4'-(trans-2-octenyloxy)cyclohexyl]benzonitrile
4-[Trans-4'-(trans-3-octenyloxy)cyclohexyl]benzonitrile
4-[Trans-4'-(trans-4-octenyloxy)cyclohexyl]benzonitrile
4-[Trans-4'-(trans-5-octenyloxy)cyclohexyl]benzonitrile
4-[Trans-4'-(trans-6-octenyloxy)cyclohexyl]benzonitrile
4-[Trans-4'-(7-octenyloxy)cyclohexyl]benzonitrile Case of n=1 in the formula (I)

4[Trans-4'-(vinyloxymethyl)cyclohexyl]benzonitrile
4-[Trans-4'-(trans-1-propenyloxymethyl)cyclohexyl]benzonitrile
4-[Trans-4'-(allyloxymethyl)cyclohexyl]benzonitrile
4-[Trans-4'-(trans-1-butenyloxymethyl)cyclohexyl]benzonitrile 4-[Trans-4'-(trans-2-butenyloxymethyl)cyclohexyl]benzonitrile
4-[Trans-4'-(3-butenyloxymethyl)cyclohexyl]benzonitrile
4-[Trans-4'-(trans-1-pentenyloxymethyl)cyclohexyl]benzonitrile
4-[Trans-4'-(trans-2-pentenyloxymethyl)cyclohexyl]benzonitrile
4-[Trans-4'-(trans-3-pentenyloxymethyl)cyclohexyl]benzonitrile
4-[Trans-4'-(4-pentenyloxymethyl)cyclohexyl]benzonitrile
4-[Trans-4'-(trans-1-hexenyloxymethyl)cyclohexyl]benzonitrile
4-[Trans-4'-(trans-2-hexenyloxymethyl)cyclohexyl]benzonitrile
4-[Trans-4'-(trans-3-hexenyloxymethyl)cyclohexyl]benzonitrile
4-[Trans-4'-(trans-4-hexenyloxymethyl)cyclohexyl]benzonitrile
4-[Trans-4'-(5-hexenyloxymethyl)cyclohexyl]benzonitrile
4-[Trans-4'-(trans-1-heptenyloxymethyl)cyclohexyl]benzonitrile
4-[Trans-4'-(trans-2-heptenyloxymethyl)cyclohexyl]benzonitrile
4-[Trans-4'-(trans-3-heptenyloxymethyl)cyclohexyl]benzonitrile
4-[Trans-4'-(trans-4-heptenyloxymethyl)cyclohexyl]benzonitrile
4-[Trans-4'-(trans-5-heptenyloxymethyl)cyclohexyl]benzonitrile
4-[Trans-4'-(6-heptenyloxymethyl)cyclohexyl]benzonitrile
4-[Trans-4'-(trans-1-octenyloxymethyl)cyclohexyl]benzonitrile
4-[Trans-4'-(trans-2-octenyloxymethyl)cyclohexyl]benzonitrile
4-[Trans-4'-(trans-3-octenyloxymethyl)cyclohexyl]benzonitrile
4-[Trans-4'-(trans-4-octenyloxymethyl)cyclohexyl]benzonitrile
4-[Trans-4'-(trans-5-octenyloxymethyl)cyclohexyl]benzonitrile
4-[Trans-4'-(trans-6-octenyloxymethyl)cyclohexyl]benzonitrile
4-[Trans-4'-(7-octenyloxymethyl)cyclohexyl]benzonitrile Case of n=2 in the formula [I]

4-[Trans-4'-(vinyloxyethyl)cyclohexyl]benzonitrile
4-[Trans-4'-(trans-1-propenyloxyethyl)cyclohexyl]benzonitrile
4-[Trans-4'-(allyloxyethyl)cyclohexyl]benzonitrile
4-[Trans-4'-(trans-1-butenyloxyethyl)cyclohexyl]benzonitrile
4-[Trans-4'-(trans-2-butenyloxyethyl)cyclohexyl]benzonitrile
4-[Trans-4'-(3-butenyloxyethyl)cyclohexyl]benzonitrile
4-[Trans-4'-(trans-1-pentenyloxyethyl)cyclohexyl]benzonitrile
4-[Trans-4'-(trans-2-pentenyloxyethyl)cyclohexyl]benzonitrile
4-[Trans-4'-(trans-3-pentenyloxyethyl)cyclohexyl]benzonitrile
4-[Trans-4'-(4-pentenyloxyethyl)cyclohexyl]benzonitrile
4-[Trans-4'-(trans-1-hexenyloxyethyl)cyclohexyl]benzonitrile
4-[Trans-4'-(trans-2-hexenyloxyethyl)cyclohexyl]benzonitrile
4-[Trans-4'-(trans-3-hexenyloxyethyl)cyclohexyl]benzonitrile
4-[Trans-4'-(trans-4-hexenyloxyethyl)cyclohexyl]benzonitrile
4-[Trans-4'-(5-hexenyloxyethyl)cyclohexyl]benzonitrile
4-[Trans-4'-(trans-1-heptenyloxyethyl)cyclohexyl]benzonitrile
4-[Trans-4'-(trans-2-heptenyloxyethyl)cyclohexyl]benzonitrile
4-[Trans-4'-(trans-3-heptenyloxyethyl)cyclohexyl]benzonitrile
4-[Trans-4'-(trans-4-heptenyloxyethyl)cyclohexyl]benzonitrile
4-[Trans-4'-(trans-5-heptenyloxyethyl)cyclohexyl]benzonitrile
4-[Trans-4'-(6-heptenyloxyethyl)cyclohexyl]benzonitrile
4-[Trans-4'-(trans-1-octenyloxyethyl)cyclohexyl]benzonitrile
4-[Trans-4'-(trans-2-octenyloxyethyl)cyclohexyl]benzonitrile
4-[Trans-4'-(trans-3-octenyloxyethyl)cyclohexyl]benzonitrile
4-[Trans-4'-(trans-4-octenyloxyethyl)cyclohexyl]benzonitrile
4-[Trans-4'-(trans-5-octenyloxyethyl)cyclohexyl]benzonitrile
4-[Trans-4'-(trans-6-octenyloxyethyl)cyclohexyl]benzonitrile
4-[Trans-4'-(7-octenyloxyethyl)cyclohexyl]benzonitrile Case of n=3 in the formula (I)

4-[Trans-4'-(vinyloxypropyl)cyclohexyl]benzonitrile
4-[Trans-4'-(trans-1-propenyloxypropyl)cyclohexyl]benzonitrile
4-[Trans-4'-(allyloxypropyl)cyclohexyl]benzonitrile
4-[Trans-4'-(trans-1-butenyloxypropyl)cyclohexyl]benzonitrile
4-[Trans-4'-(trans-2-butenyloxypropyl)cyclohexyl]benzonitrile
4-[Trans-4'-(3-butenyloxypropyl)cyclohexyl]benzonitrile
4-[Trans-4'-(trans-1-pentenyloxypropyl)cyclohexyl]benzonitrile
4-[Trans-4'-(trans-2-pentenyloxypropyl)cyclohexyl]benzonitrile
4-[Trans-4'-(trans-3-pentenyloxypropyl)cyclohexyl]benzonitrile
4-[Trans-4'-(4-pentenyloxypropyl)cyclohexyl]benzonitrile
4-[Trans-4'-(trans-1-hexenyloxypropyl)cyclohexyl]benzonitrile
4-[Trans-4'-(trans-2-hexenyloxypropyl)cyclohexyl]benzonitrile
4-[Trans-4'-(trans-3-hexenyloxypropyl)cyclohexyl]benzonitrile
4-[Trans-4'-(trans-4-hexenyloxypropyl)cyclohexyl]benzonitrile
4-[Trans-4'-(5-hexenyloxypropyl)cyclohexyl]benzonitrile
4-[Trans-4'-(trans-1-heptenyloxypropyl)cyclohexyl]benzonitrile
4-[Trans-4'-(trans-2-heptenyloxypropyl)cyclohexyl]benzonitrile 4-[Trans-4'-(trans-3-heptenyloxypropyl)cyclohexyl]-benzonitrile
4-[Trans-4'-(trans-4-heptenyloxypropyl)cyclohexyl]-benzonitrile
4-[Trans-4'-(trans-5-heptenyloxypropyl)cyclohexyl]-benzonitrile
4-[Trans-4'-(6-heptenyloxypropyl)cyclohexyl]benzonitrile
4-[Trans-4'-(trans-1-octenyloxypropyl)cyclohexyl]benzonitrile
4-[Trans-4'-(trans-2-octenyloxypropyl)cyclohexyl]benzonitrile
4-[Trans-4'-(trans-3-octenyloxypropyl)cyclohexyl]benzonitrile
4-[Trans-4'-(trans-4-octenyloxypropyl)cyclohexyl]benzonitrile
4-[Trans-4'-(trans-5-octenyloxypropyl)cyclohexyl]benzonitrile
4-[Trans-4'-(trans-6-octenyloxypropyl)cyclohexyl]benzonitrile
4-[Trans-4'-(7-octenyloxypropyl)cyclohexyl]benzonitrile Case of n=4 in the formula (I)

4-[Trans-4'-(vinyloxybutyl)cyclohexyl]benzonitrile
4-[Trans-4'-(trans-1-propenyloxybutyl)cyclohexyl]benzonitrile
4-[Trans-4'-(allyloxybutyl)cyclohexyl]benzonitrile
4-[Trans-4'-(trans-1-butenyloxybutyl)cyclohexyl]benzontrile
4-[Trans-4'-(trans-2-butenyloxybutyl)cyclohexyl]benzontrile
4-[Trans-4'-(3-butenyloxybutyl)cyclohexyl]benzonitrile
4-[Trans-4'-(trans-1-pentenyloxybutyl)cyclohexyl]benzonitrile
4-[Trans-4'-(trans-2-pentenyloxybutyl)cyclohexyl]benzonitrile
4-[Trans-4'-(trans-3-pentenyloxybutyl)cyclohexyl]benzonitrile
4-[Trans-4'-(4-pentenyloxybutyl)cyclohexyl]benzonitrile
4-[Trans-4'-(trans-1-hexenyloxybutyl)cyclohexyl]benzonitrile
4-[Trans-4'-(trans-2-hexenyloxybutyl)cyclohexyl]benzonitrile
4-[Trans-4'-(trans-3-hexenyloxybutyl)cyclohexyl]benzonitrile
4-[Trans-4'-(trans-4-hexenyloxybutyl)cyclohexyl]benzonitrile
4-[Trans-4'-(5-hexenyloxybutyl)cyclohexyl]benzonitrile
4-[Trans-4'-(trans-1-heptenyloxybutyl)cyclohexyl]benzonitrile
4-[Trans-4'-(trans-2-heptenyloxybutyl)cyclohexyl]benzonitrile
4-[Trans-4'-(trans-3-heptenyloxybutyl)cyclohexyl]benzonitrile
4-[Trans-4'-(trans-4-heptenyloxybutyl)cyclohexyl]benzonitrile
4-[Trans-4'-(trans-5-heptenyloxybutyl)cyclohexyl]benzonitrile
4-[Trans-4'-(6-heptenyloxybutyl)cyclohexyl]benzonitrile
4-[Trans-4'-(trans-1-octenyloxybutyl)cyclohexyl]benzonitrile
4-[Trans-4'-(trans-2-octenyloxybutyl)cyclohexyl]benzonitrile
4-[Trans-4'-(trans-3-octenyloxybutyl)cyclohexyl]benzonitrile
4-[Trans-4'-(trans-4-octenyloxybutyl)cyclohexyl]benzonitrile
4-[Trans-4'-(trans-5-octenyloxybutyl)cyclohexyl]benzonitrile
4-[Trans-4'-(trans-6-octenyloxybutyl)cyclohexyl]benzonitrile
4-[Trans-4'-(7-octenyloxybutyl)cyclohexyl]benzonitrile The compound of the present invention does not always exhibit liquid crystal phases in the form of a single substance, but it is stable to environmental factors (moisture, heat, air, light, electricity, etc.) and colorless and also superior in compatibility with other liquid crystal compounds such as existing liquid crystalline compounds e.g. esters, Schiff's compounds, ethane compounds, azoxy compounds, biphenyls, cyclohexanes, pyridines, pyrimidines, etc.; hence when the compound of the present invention is mixed with these compounds or mixtures thereof, it is possible to formulate the compound into liquid crystal materials suitable to various use applications. Further, the compound of the present invention has a large dielectric anisotropy value ($\Delta\epsilon$) and high elastic constant ratios of $K_{33}/K_{11}$ and $K_{33}/K_{22}$.

The preparation of the present invention will be illustrated below.

The compound of the formula (I) of the present invention may be prepared according to the following equations:

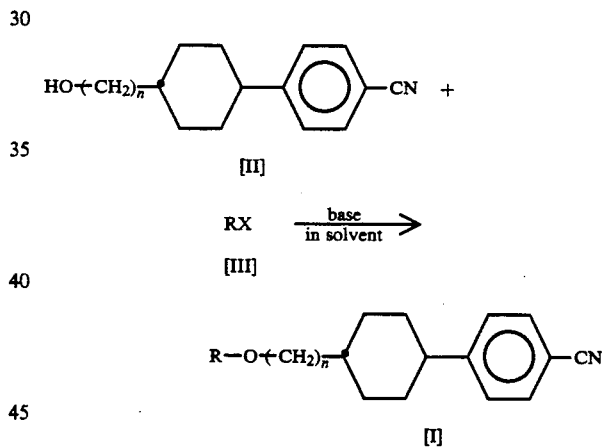

wherein R represents an alkenyl group of 2 to 8 carbon atoms, X represents chlorine, bromine, iodine or other leaving groups, preferably tosyloxy group or mesyloxy group.

Namely, the compound of the invention may be prepared by treating a [4-trans-(4'-cyanophenyl)cyclohexyl]alkanol [II] and compound (III) with a base in a solvent. Examples of such a base are sodium amide, pottasium carbonate, triethylamine, sodium hydroxide, barium oxide, silver oxide, sodium hydride, sodium methoxide, potassium t-butoxide, etc. Examples of such a solvent are dimethyl sulfoxide, dimethylformamide, dimethoxyethane, tetrahydrofuran, etc.

The compound (II) as a starting material may be obtained by reducing 4-(4'-cyanophenyl)cyclohexanone in the case of n=0. As a reducing agent in this case, lithium aluminum hydride, bis(methoxyethoxy)aluminumsodium hydride, tri-t-butoxy lithium aluminum hydride, lithium borohydride, potassium borohydride, sodium borohydride, sodium borocyanohydride, diborane, diisobutylaluminum hydride, aluminum hydride, tributyltin hydride, etc. are exemplified. Among these, tri-t-butoxy lithium aluminum hydride, lithiumbrohydride, potassium borohydride, sodium borohydride and sodium borocyanohydride are preferred.

Further, a compound in the case of n=1 in the formula (II), i.e. compound (IIa) may be prepared according to the following equation:

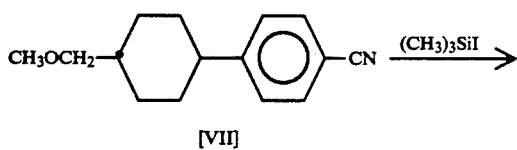

[VII]

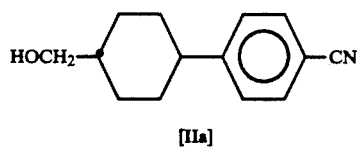

[IIa]

Namely, compound (IIa) is obtained by reacting trans-4-methoxymethyl-1-(4'-cyanophenyl)cyclohexane (VII) with trimethylsilyl iodide. Herein, compound (VII) is a known substance and may be prepared for example according to the method disclosed in Japanese patent application laid-open No. Sho 58-59956/1983 of the present inventors. The compound (IIa) may also be prepared by extending the carbon number of 4-(4'-cyanophenyl)cyclohexanone Compounds in the case of n=2 to 4 in the formula (II) may also be prepared by extending the carbon number of compound (IIa).

The compound of the formula (I) of the present invention may also be prepared through the following route:

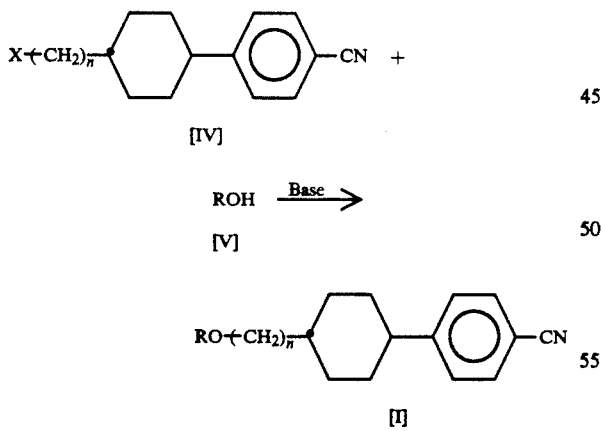

wherein R is as defined above and X represents Cl, Br, I or other leaving groups, preferably tosyloxy group or mesyloxy group.

Namely, the compound of the formula (I) may be prepared by treating compound (IV) and an alkenyl alcohol (V) with the same base and solvent as those used in the above method.

The compound of the formula (I) may also be prepared according to the following method:

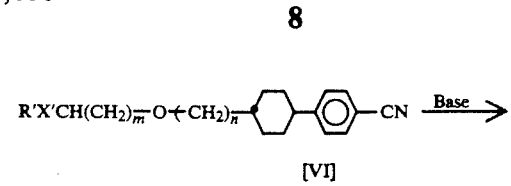

[VI]

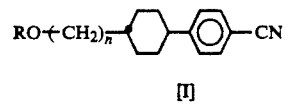

[I]

wherein R' represents hydrogen atom or an alkyl group of 1 to 7 carbon atoms, X' represents F, Cl, Br or I, m represents 0 to 7 and R is defined above.

Namely, compound (I) is obtained by treating compound [VI] with a base. Examples of such a base are potassium t-butoxide, 1,8-diazabicyclo(5.4.0) undec-7-ene, sodium hydroxide, potassium hydroxide, sodium methoxide, pyridine, silver oxide, etc.

The liquid crystal composition of the present invention is characterized by comprising at least two liquid crystals or liquid crystalline compounds, at least one of which is a liquid crystalline compound expressed by the above formula (I).

As compounds in admixture with the compound of the formula (I), as a component of the liquid crystal composition of the present invention, the following known liquid crystalline compounds expressed by the formulas (i) to (xxxiii) may be used:

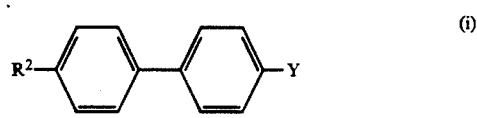
(i)

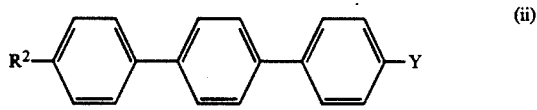
(ii)

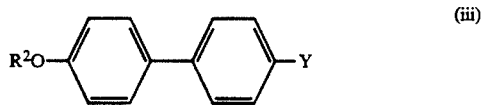
(iii)

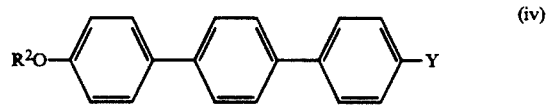
(iv)

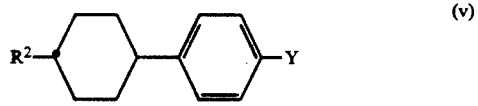
(v)

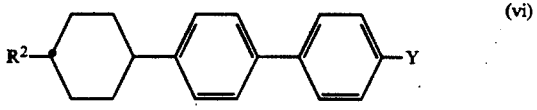
(vi)

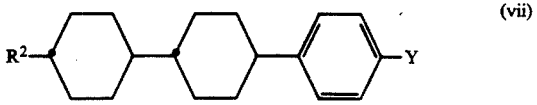
(vii)

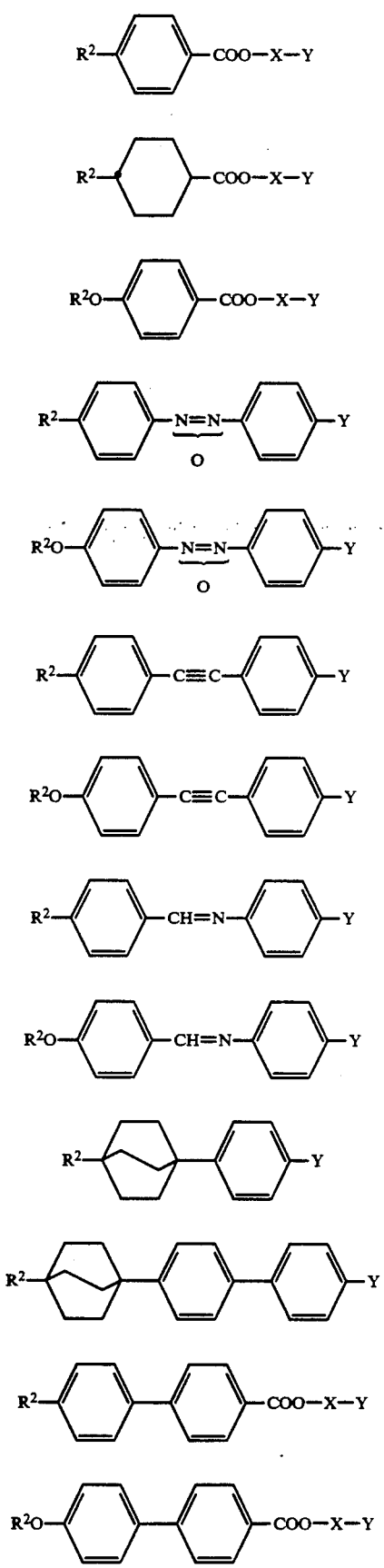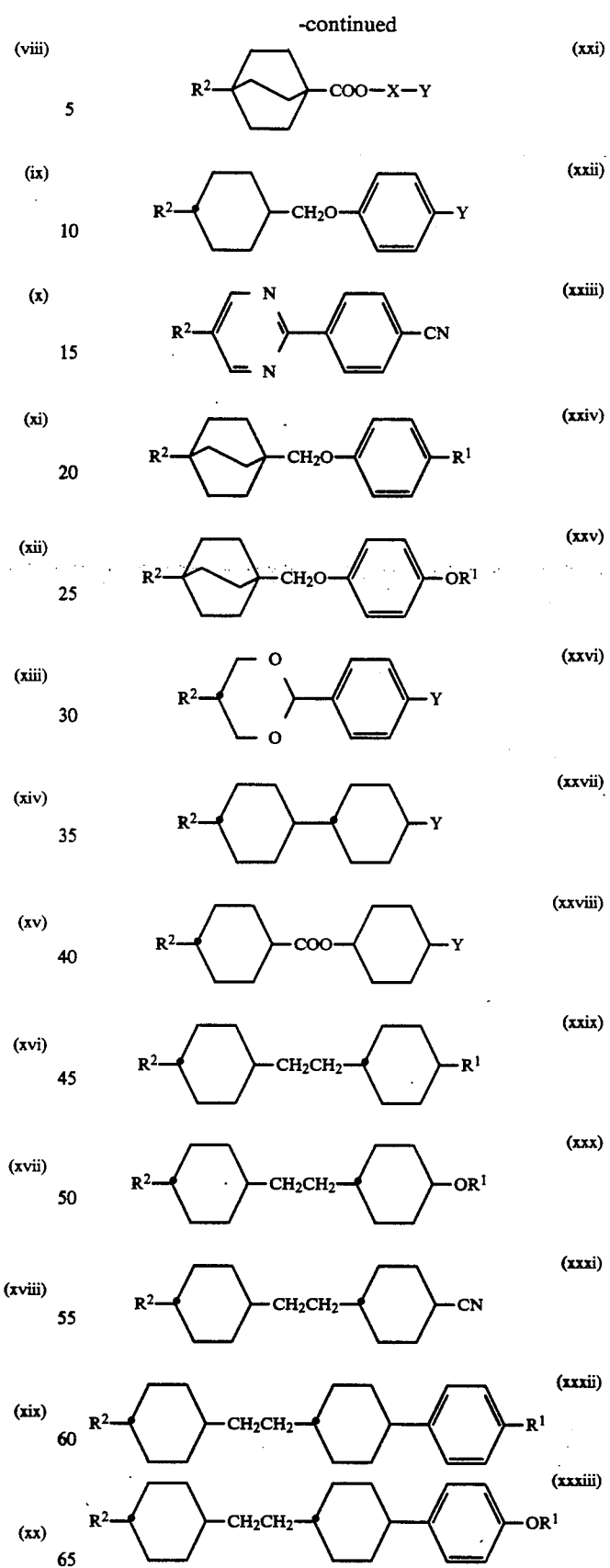
In the formulas (i) to (xxxiii), x represents

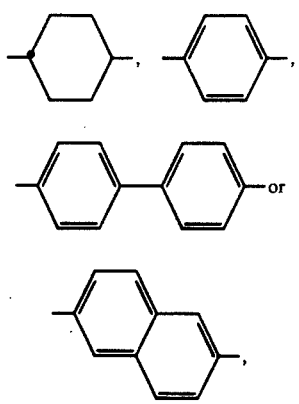

Y represents —CN, a halogen atom, $R^1$ or $OR^1$ and $R^2$ and $R^1$ each represent a linear alkyl group of 1 to 10 carbon atoms.

The present invention will be described in more detail by way of Examples, but it should not be construed to be limited thereto.

The symbols C-N point and N-I point in Examples mean crystal-nematic phase transition point and nematic phase-isotropic liquid phase transition point, respectively.

EXAMPLE 1

Preparation of 4-[trans-4'-(allyloxymethyl)cyclohexyl]benzonitrile (a compound of the formula (I) wherein R represents $CH_2=CHCH_2$— and n represents 1)

Tetrahydrofuran (100 ml) was dropwise added into a 500 ml capacity three-necked flask containing sodium hydride (1.8 g, 0.08 mol), followed by cooling the flask down to 10° C., dropwise adding a solution of [trans-4-(4'-cyanophenyl)cyclohexyl]methanol (10.8 g, 0.05 mol) in tetrahydrofuran (50 ml), agitating these at 10° C. for 30 minutes, adding a solution of allyl bromide (9.1 g, 0.08 mol) in tetrahydrofuran (30 ml), agitating these at room temperature for 4 hours, thereafter adding water and toluene (each, 100 ml), removing the resulting aqueous layer, three times washing the organic layer with water (100 ml), drying it over magnesium sulfate, filtering off the drying agent, concentrating the layer under reduced pressure to obtain an oily substance (17.8 g), purifying it according to silica gel column chromatography (using toluene solvent), twice recrystallizing the resulting substance from alcohol and drying to obtain the captioned compound (1.2 g, 0.005 mol). This product had a m.p. of 17.0°–17.9° C. and its NMR spectra indicated that the product was the captioned compound.

EXAMPLE 2

Preparation of 4-[trans-4'-(3-butenyloxymethyl)cyclohexyl]benzonitrile (a compound of the formula (I) wherein R represents $CH_2=CH(CH_2)2$— and n represents 1)

Into a 100 ml capacity three-necked flask were added trans-4-(4'-cyanophenyl)cyclohexanecarboxyaldehyde (2.1 g, 0.01 mol), 3-buten-1-ol (5.2 ml) and triethylsilane (1.8 ml), followed by agitating these, cooling down to 0° C., adding trifluoroacetic acid (4.6 ml), agitating these at 5° C. for 30 minutes, adding water (30 ml) and toluene (30 ml), removing the resulting aqueous layer, washing the toluene solution with 2N-NaOH solution, further washing with water till the washing water became neutral, drying the solution over magnesium sulfate, removing magnesium sulfate, distilling off toluene in vacuo to obtain a colorless oily substance (3.9 g) and purifying it according to silica gel column chromatography (using toluene solvent) to obtain the objective 4-[trans-4'-(3-butenyloxymethyl)cyclohexyl]benzonitrile (0.3 g). The NMR spectra of the resulting compound indicated that the compound was the captioned one, and its m.p. was 12.7°–13 4° C.

EXAMPLE 3

Preparation of 4-[trans-4'-(allyloxy)cyclohexyl]benzonitrile (a compound of the formula (I) wherein R represents $CH_2=CHCH_2$— and n represents 0)

(i) Preparation of trans-4-phenylcyclohexanol

Tetrahydrofuran (200 ml) was dropwise added into a 1 l capacity three-necked flask containing lithiumaluminum hydride (9.9 g, 0.26 mol), at 0° C., followed by sufficiently suspending these materials, dropwise adding a solution of phenylcyclohexanone (91.3 g, 0.52 mol) in tetrahydrofuran (200 ml), agitating the mixture at room temperature for 2 hours, again cooling it down to 0° C., dropwise adding ethyl acetate (20 ml), further adding dilute hydrochloric acid (100 ml), removing insolubles in the resulting reaction solution by suction-filtration, adding ethyl acetate (100 ml) to the filtrate for extraction, three times washing the resulting organic layer with water (100 ml), drying it over magnesium sulfate, filtering off magnesium sulfate, concentrating the residue under reduced pressure to obtain white crystals (98.5 g), recrystallizing from alcohol and drying to obtain 4-trans-phenylcyclohexanol (55 g). M.P.: 117°–119° C.

(ii) Preparation of 4-[trans-4'-(acetyloxy)cyclohexyl]iodobenzene

Into a 100 ml capacity three-necked flask were added the compound obtained in the above item (i) (8.8 g, 0.05 mol), acetic acid (35 ml), water (10 ml), iodic acid (2.1 g, 0.01 mol), iodine (5.6 g, 0.02 mol), carbon tetrachloride (4 ml) and sulfuric acid (1.4 ml), followed by agitating these under reflux for 8 hours, cooling down to room temperature after completion of the reaction, adding a 10% aqueous solution of sodium thiosulfate (2 ml), adding toluene (100 ml), transferring the mixture into a separating funnel, washing the resulting toluene layer with water till the washing water became neutral, distilling off toluene under reduced pressure, passing the residue through a silica gel layer filled in a column using n-heptane solvent, concentrating the n-heptane solution having passed through the silica gel layer under reduced pressure, recrystallizing the resulting oily substance (12.4 g) from alcohol and drying to obtain 4-[trans-4'-(acetyloxy)cyclohexyl]iodobenzene (3.7 g). M.P.: 84.4°–85.4° C. NMR spectra also indicated the compound.

(iii) Preparation of 4-[trans-4'-(acetyloxy)cyclohexyl]benzonitrile

Into a 100 ml capacity three-necked flask were added the compound obtained in the above item (ii) (3.7 g, 0.01 mol), cuprous cyanide (1.2 g, 0.012 mol) and N,N-dimethylformamide (15 ml), followed by agitating the mixture under reflux for 6 hours, cooling down to room temperature, adding a 28% aqueous ammonia (4 ml) and toluene (50 ml) for extraction, washing the resulting organic layer with 6N-hydrochloric acid (30 ml), further washing with 2N-NaOH aqueous solution (30 ml), washing with water till the washing water became neutral, drying the toluene layer over anhydrous magnesium sulfate, removing the drying agent, distilling off toluene under reduced pressure to obtain white crystals, recrystallizing from carbon tetrachloride and drying to obtain 4-[trans-4'-(acetyloxy)cyclohexyl]benzonitrile (2.3 g). M.P.: 130.2°–130.9° C. NMR spectra also indicated the compound.

(iv) Preparation of 4-[trans-4'-(hydroxy)cyclohexyl]benzonitrile

Into a 100 ml capacity three-necked flask were added the compound obtained in the item (iii) (2.3 g, 0.01 mol), potassium carbonate (1.4 g, 0.01 mol), methanol (30 ml) and water (30 ml), followed by agitating the mixture at 60° C. for one hour, adding ethyl acetate (30 ml) for extraction, three times washing the resulting organic layer with water (30 ml), drying the organic layer over anhydrous magnesium sulfate, removing the drying agent, distilling off ethyl acetate under reduced pressure to obtain white crystals (1.5 g), recrystallizing from a mixed solvent of n-heptane with ethyl acetate and drying to obtain the captioned compound (1.4 g). M.P.: 121.0°–122.4° C.

(v) Preparation of 4-[Trans-4'-(allkyloxy)cyclohexyl]benzonitrile

The captioned compound was obtained in the same manner as in Example 1. M.P.: 92.9°–93.8° C.

EXAMPLE 4

Composition

A nematic liquid crystal composition A consisting of

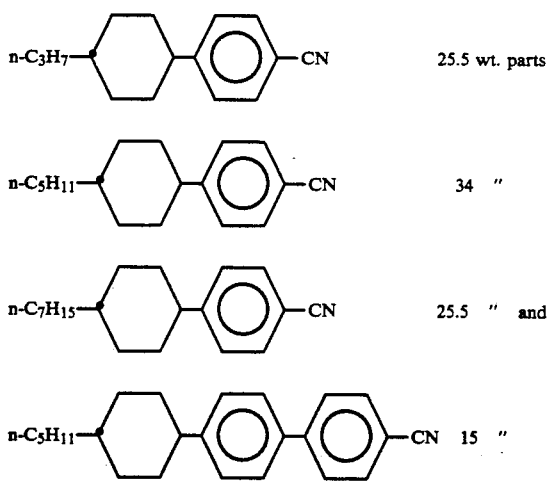

| | |
|---|---|
| n-C₃H₇—⟨⟩—⟨⟩—CN | 25.5 wt. parts |
| n-C₅H₁₁—⟨⟩—⟨⟩—CN | 34 " |
| n-C₇H₁₅—⟨⟩—⟨⟩—CN | 25.5 " and |
| n-C₅H₁₁—⟨⟩—⟨⟩—⟨⟩—CN | 15 " | exhibited a N-I point of 72.4° C., a dielectric anisotropy value $\Delta\epsilon$ of 11.0 ($\epsilon_\parallel = 15.4$, $\epsilon_\perp = 4.4$), a viscosity at 20° C. of 27.5 cp, an optical anisotropy value $\Delta n$ of 0.137, a threshold voltage of 1.78 V, a ratio of elastic constants of $K_{33}/K_{11}$ of 1.94 and that of $K_{33}/K_{22}$ of 2.95. A liquid crystal composition obtained by adding 4-[trans-4'-(allkyloxymethyl)cyclohexyl]benzonitrile (15 parts by wt.) shown in Example 1 of the present invention (a compound of the present invention) to the above nematic liquid crystal composition A exhibited a dielectric anisotropy value $\Delta\epsilon$ raised up to 11.6 ($\epsilon_\parallel = 16.7$, $\epsilon_\perp = 5.1$) and a threshold voltage lowered down to 1.51 V to thereby make it possible to drive liquid crystal display devices at a lower voltage, and the ratios of elastic constants $K_{33}/K_{11}$ and $K_{33}/K_{22}$ increased up to 2.35 and 3.06, respectively, and the steepness of voltage-transmittance characteristic was improved.

COMPARATIVE EXAMPLE

To the above nematic liquid crystal composition A was added 4-[trans-4'-(3-butenyl)cyclohexyl]benzonitrile which has been regarded as one of compounds having the best steepness of $\gamma$ characteristic (15 parts by weight). The resulting liquid crystal composition had a $K_{33}/K_{11}$ of 2.21 and a $K_{33}/K_{22}$ of 2.95. Thus, when these values were compared with those shown in Example 4, the values of $K_{33}/K_{11}$ and $K_{33}/K_{22}$ were lower than those of Example 4.

EXAMPLE 5

Composition

To the nematic liquid crystal composition A used in Example 4 was added 4-[trans-4'-(3-butenyloxymethyl)cyclohexyl]benzonitrile shown in Example 2 ( a compound of the present invention)(15 parts by wt.). The resulting liquid crystal composition exhibited a $\Delta\epsilon$ of 11.3, a $\Delta n$ of 0.129 and a viscosity at 20° C. of 28.2 cp, and the ratios of elastic constants, $K_{33}/K_{11}$ and $K_{33}/K_{22}$ were 2.18 and 2.93, respectively.

EXAMPLE 6

Preparation of 4-{trans-4'-(trans-2-butenyloxymethyl)cyclohexyl}benzonitrile (i) Preparation of 4-{trans-4'-(p-toluenesulfonyloxymethyl)cyclohexyl}benzonitrile Into a 1 l capacity three-necked flask were added 4-{trans-4'-(hydroxymethyl)cyclohexyl}benzonitrile (75.6 g, 0.35 mol) and pyridine (150 ml), followed by cooling these down to 0° C., dropwise adding a pyridine solution (150 ml) of p-toluenesulfonyl chloride (70.3 g, 0.37 mol) over one hour, agitating these at room temperature for 2 hours, allowing them to stand overnight, adding water (500 ml), extracting with toluene, three times washing with water (300 ml), drying over magnesium sulfate, removing magnesium sulfate, concentrating the residue, passing it through a silica gel column using a chloroform solution, distilling off chloroform, recrystallizing from a mixed solvent of n-heptane with ethyl acetate and drying to obtain white crystals (103.5 g). The NMR spectra of this product accorded with those of the captioned compound and its M.P. was 108.1°–110.5° C.

(ii) Preparation of 4-{trans-4'-(trans-2-butenyloxymethyl)cyclohexyl}benzonitrile Into a 200 ml capacity three-necked flask were added sodium hydride (2.9 g, 0.055 mol), trans-2-buten-1-ol (3.6 g, 0.05 mol) and tetrahydrofuran (50 ml), followed by agitating these for one hour, dropwise adding a tetrahydrofuran solution (50 ml) of 4-{trans-4'-(p-toluenesulfonyloxymethyl)cyclohexyl}benzonitrile (18.5 g, 0.05 mol) obtained in the above item (i), heating the mixture under reflux for 3 hours, cooling down to room temperature, adding cold dilute hydrochloric acid, extracting with toluene, adding 2N-NaOH (100 ml), separating the toluene solution, washing with water till the washing water became neutral, drying over magnesium sulfate, removing magnesium sulfate, concentrating the residue under reduced pressure and purifying according to silica gel column chromatography using toluene solvent to obtain the captioned compound (1.9 g). This product was liquid at room temperature.

EXAMPLE 7

Preparation of 4-{trans-4'-(2-allyloxyethyl)cyclohexyl}benzonitrile (i) Preparation of 4-{trans-4'-(formyl)cyclohexyl}benzonitrile Into a 3 l capacity three-necked flask were added pyridium chlorochromate (161.7 g, 0.75 mol) and dichloromethane(1,000 ml), followed by agitating these, adding a dichloromethane solution (800 ml) of 4-{trans-4'-(hydroxymethyl)cyclohexyl}benzonitrile(107.6 g, 0.5 mol) at 20° C., agitating these for 90 minutes while keeping the temperature at 20° C., adding diethyl ether (1,500 ml), decanting the supernatant, passing the supernatant through a Florisil (trademark of the Floridin Company) column, concentrating under reduced pressure to obtain the captioned compound (101.2 g). Its structure was confirmed according to NMR spectra.

(ii) Preparation of 4-{trans-4'-(2-methoxyethenyl)cyclohexyl}benzonitrile

Into a 3 l capacity three-necked flask were added methoxymethyltriphenylphosphonium chloride (236.1 g, 0.7 mol) and t-butyl methyl ether (700 ml), followed by cooling these down to $-10°$ C., adding potassium t-butoxide (77.3 g, 0.7 mol), agitating these at 0° C. for one hour, again cooling down to $-10°$ C., dropwise adding a solution of the compound obtained in the above item (i) (101.2 g) in t-butyl methyl ether (300 ml), agitating these at 0° C. for 4 hours, adding water (500 ml), separating an organic layer, washing it with water till the washing water became neutral, drying over magnesium sulfate, removing magnesium sulfate, concentrating the residue under reduced pressure, adding heptane (500 ml) for recrystallization, filtering off the resulting crystals, concentrating the filtrate under reduced pressure, passing the concentrate through a silica gel column using heptane solvent and concentrating under reduced pressure to obtain the captioned compound (90.2 g).

(iii) Preparation of 4-{trans-4'-(formylmethyl)cyclohexyl}benzonitrile

Into a 1 l capacity three-necked flask were added the compound obtained in the above item (ii) (36.2 g, 0.15 mol), 2N-hydrochloric acid (142 ml) and tetrahydrofuran (560 ml), followed by refluxing these for one hour, distilling off tetrahydrofuran, adding water (100 ml) to extract with ethyl acetate, washing the extract with 1N-NaOH aqueous solution, washing with water till the washing water became neutral, drying over magnesium sulfate, removing magnesium sulfate, concentrating under reduced pressure, recrystallizing from a mixed solvent of heptane with ethyl acetate and drying to obtain white crystals (20.5 g). The NMR spectra of this product accorded with those of the captioned compound.

(iv) Preparation of 4-{trans-4'-(hydroxyethyl)cyclohexyl}benzonitrile

Into a 500 ml capacity three-necked flask were added sodium borohydride (3.4 g, 0.09 mol) and isopropyl alcohol (50 ml), followed by cooling these down to 10° C., dropwise adding an isopropyl alcohol solution (100 ml) of the compound obtained in the above item (iii) (20.5 g, 0.09 mol), agitating these at room temperature for 2 hours, adding cold dilute sulfuric acid (100 ml), extracting the mixture with ethyl acetate, washing the organic layer with 1N-NaOH solution, washing with water till the washing water became neutral, drying over magnesium sulfate, removing magnesium sulfate and concentrating the residue under reduced pressure to obtain crystals (20.6 g), recrystallizing from a mixed solvent of heptane with ethyl acetate and drying to obtain white crystals (13.4 g). The NMR spectra of this product accorded with those of the captioned compound.

(v) Preparation of 4-{trans-4'-(2-allyloxyethyl)cyclohexyl}benzonitrile

The captioned compound was obtained in the same manner as in Example 1. M.P.: 38.0°–38.4° C.

EXAMPLE 8

Preparation of 4-{trans-4'-(3-allyloxypropyl)cyclohexyl}benzonitrile (a compound of the formula (I) wherein R represents $CH_2=CHCH_2-$ and n represents 3)

The compound (iii) of Example 7 was subjected to the procedures of (ii), (iii), (iv) and (v) of Example 7 in this order to obtain the captioned compound. M.P.: 12.0° C., N-I point: 5.9° C.

EXAMPLE 9

Preparation of 4-{trans-4'-(4-allyloxybutyl)cyclohexyl}benzonitrile (a compound of the formula (I) wherein R represents $CH_2=CHCH_2-$ and n represents 4)

4-{Trans-4'-(2-formylethyl)cyclohexyl}benzonitrile obtained as an intermediate in Example 8 was subjected to the same procedure as in Example 8 to obtain the captioned compound. M.P.: 30° C.

EXAMPLE 10

Preparation of 4-{trans-4'-(trans-2-butenyloxyethyl)cyclohexyl}benzonitrile (a compound of the formula (I) wherein R represents $CH_3CH=CHCH_2-$ and n represents 2)

The compound (iv) of Example 7 was subjected to the same procedure as in Example 6 to obtain the captioned compound. M.P.: 54° C.

EXAMPLE 11

Preparation of 4-{trans-4'-(trans-2-butenyloxypropyl)cyclohexyl}benzonitrile (a compound of the formula (I) wherein R represents $CH_3CH=CHCH_2-$ and n represents 3)

4-{Trans-4'-(3-hydroxypropyl)cyclohexyl}benzonitrile obtained as an intermediate in Example 8 was subjected to the same procedure as in Example 6 to obtain the captioned compound. This product was liquid at room temperature.

EXAMPLES 12–18

Compositions

To the nematic liquid crystal composition A used in Example 4 were added the respective compounds of the formula (I) obtained in Examples 3 and 6 to 11 each in 15 parts by weight to prepare liquid crystal compositions (Examples 12–18). The ratios of elastic constants of the thus obtained liquid crystal compositions, $K_{33}/K_{11}$ and $K_{33}/K_{22}$, are shown in Table 1 together with the results of the afore-mentioned Example 4, Example 5 and Comparative example.

TABLE 1

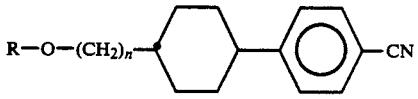

| Example (composition) | R'' | m | n | Example | $K_{33}/K_{11}$ | $K_{33}/K_{22}$ |
|---|---|---|---|---|---|---|
| 4 | H | 1 | 1 | 1 | 2.35 | 3.06 |
| 5 | H | 2 | 1 | 2 | 2.18 | 2.93 |
| 12 | H | 1 | 0 | 3 | 2.43 | 2.66 |
| 13 | CH₃ | 1 | 1 | 6 | 1.98 | 2.79 |
| 14 | H | 1 | 2 | 7 | 2.15 | 2.64 |
| 15 | H | 1 | 3 | 8 | 2.04 | 2.82 |
| 16 | H | 1 | 4 | 9 | 2.12 | 2.79 |
| 17 | CH₃ | 1 | 2 | 10 | 1.92 | 3.34 |
| 18 | CH₃ | 1 | 3 | 11 | 2.15 | 3.41 |
| Comp. ex. | 4-[Trans-4'-(3-butenyl)-cyclohexyl]benzonitrile | | | | 2.21 | 2.95 |

When the compound of the present invention is added to a nematic liquid crystal composition, the dielectric anisotropy value Δε of the resulting composition is increased and hence its threshold voltage is lowered, and further either of the ratios of elastic constants, $K_{33}/K_{11}$ and $K_{33}/K_{22}$, are raised so that the voltage-transmittance characteristics (γ characteristics) become steeper. Thus, liquid crystal compositions particularly suitable to liquid crystal display elements utilizing SBE mode are obtained.

What is claimed is:

1. An alkenyl ether compound expressed by the formula

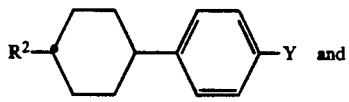

(I)

wherein R represents an alkenyl group of 2 to 8 carbon atoms having a double bond at its end or a double bond of trans configuration in any other position and n represents an integer of 0 to 4.

2. An alkenyl ether compound according to claim 1 wherein said R represents an allyl group.

3. An alkenyl ether compound according to claim 1 wherein said R represents a 3-butenyl group.

4. An alkenyl ether compound according to claim 1 wherein said R represents a trans-2-butenyl group.

5. A liquid crystal composition comprising at least two components at least one of which is an alkenyl ether compound as set forth in claim 1.

6. A liquid crystal composition comprising at least one alkenyl ether compound as set forth in claim 1 and further a nematic liquid crystal composition consisting of

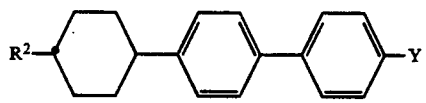

wherein Y represents —CN, a halogen atom, $R^1$ or $OR^1$ and $R^2$ and $R^1$ each represents a linear alkyl group of 1 to 10 carbon atoms.

7. A liquid crystal composition comprising at least one alkenyl ether compound as set forth in claim 1 and further a nematic liquid crystal composition consisting of

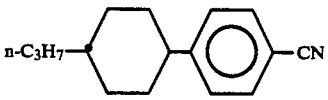

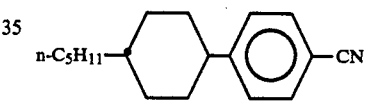

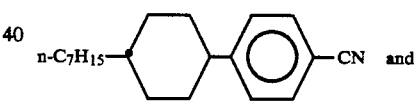

and

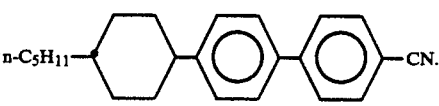

* * * * *